(12) United States Patent
Pung

(10) Patent No.: US 11,540,932 B2
(45) Date of Patent: *Jan. 3, 2023

(54) STENT AND STENT CONNECTION INTERFACE

(71) Applicant: MicroVention, Inc., Aliso Viejo, CA (US)

(72) Inventor: Ponaka Pung, Signal Hill, CA (US)

(73) Assignee: MicroVention, Inc., Tustin, CA (US)

( * ) Notice: Subject to any disclaimer, the term of this patent is extended or adjusted under 35 U.S.C. 154(b) by 250 days.

This patent is subject to a terminal disclaimer.

(21) Appl. No.: 16/920,227

(22) Filed: Jul. 2, 2020

(65) Prior Publication Data

US 2020/0330249 A1 Oct. 22, 2020

Related U.S. Application Data

(63) Continuation of application No. 16/127,136, filed on Sep. 10, 2018, now Pat. No. 10,736,760.

(60) Provisional application No. 62/563,570, filed on Sep. 26, 2017.

(51) Int. Cl.
*A61F 2/95* (2013.01)
*A61F 2/91* (2013.01)
*A61F 2/966* (2013.01)
*A61F 2/848* (2013.01)
*A61F 2/90* (2013.01)
*A61F 2/92* (2013.01)

(52) U.S. Cl.
CPC ............... *A61F 2/95* (2013.01); *A61F 2/848* (2013.01); *A61F 2/90* (2013.01); *A61F 2/91* (2013.01); *A61F 2/966* (2013.01); *A61F 2/92* (2013.01); *A61F 2002/8486* (2013.01); *A61F 2002/9505* (2013.01); *A61F 2002/9534* (2013.01)

(58) Field of Classification Search
CPC .... A61F 2/90; A61F 2/848; A61F 2/91; A61F 2/95; A61F 2/966; A61F 2002/8486; A61F 2002/9505; A61F 200/9534
See application file for complete search history.

(56) References Cited

U.S. PATENT DOCUMENTS

| | | | |
|---|---|---|---|
| 2012/0083868 A1* | 4/2012 | Shrivastava | A61F 2/844 623/1.11 |
| 2012/0277788 A1 | 11/2012 | Cattaneo | |
| 2017/0112513 A1* | 4/2017 | Marchand | A61F 2/014 |

* cited by examiner

*Primary Examiner* — Suba Ganesan
(74) *Attorney, Agent, or Firm* — Inskeep IP Group, Inc.

(57) ABSTRACT

A stent with a common connection interface, and a method and platform used to create a stent with a common connection interface is described. A common connection interface used to connect a stent to a pusher is described.

19 Claims, 18 Drawing Sheets

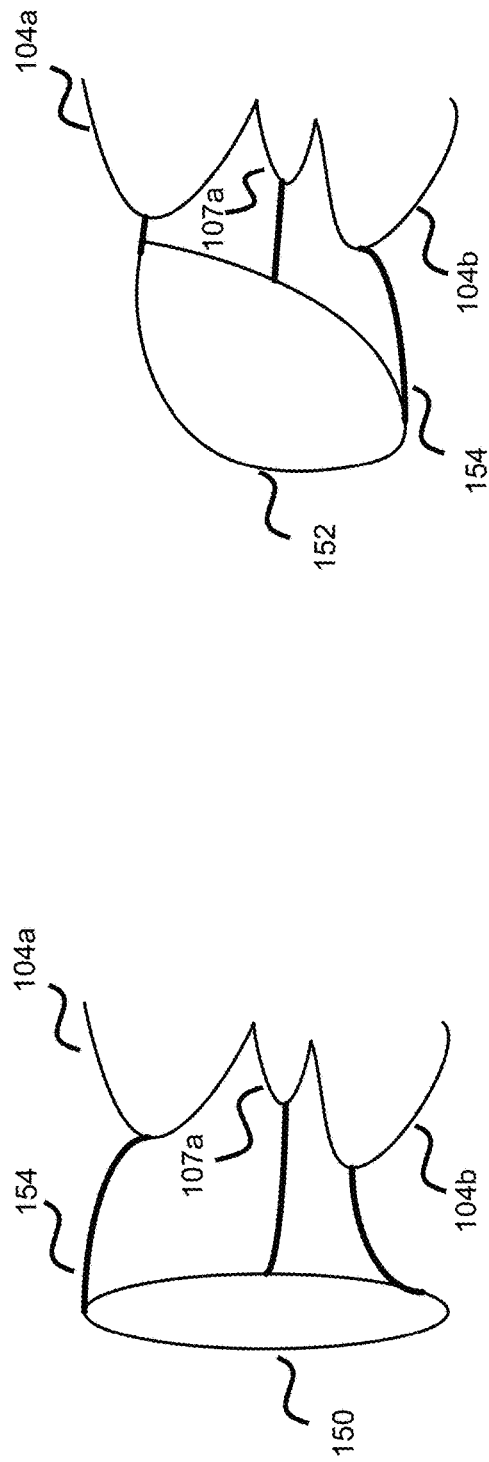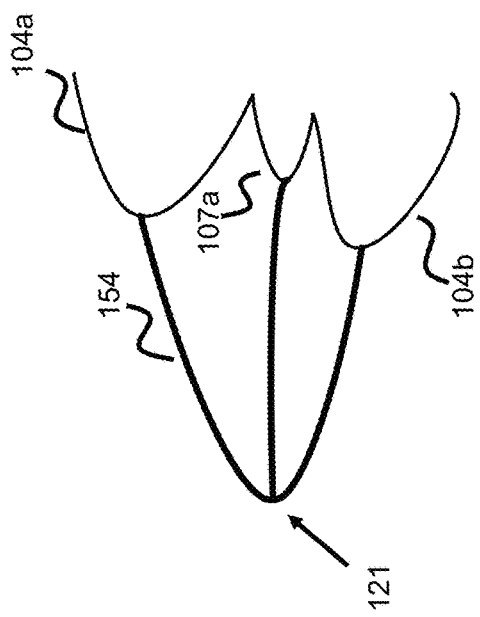
Figure 14a
Figure 14b
Figure 14c

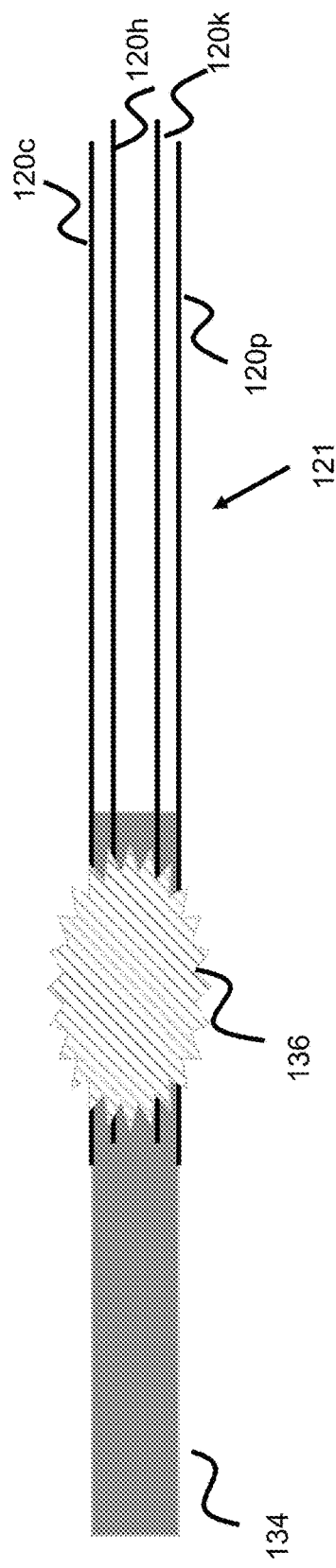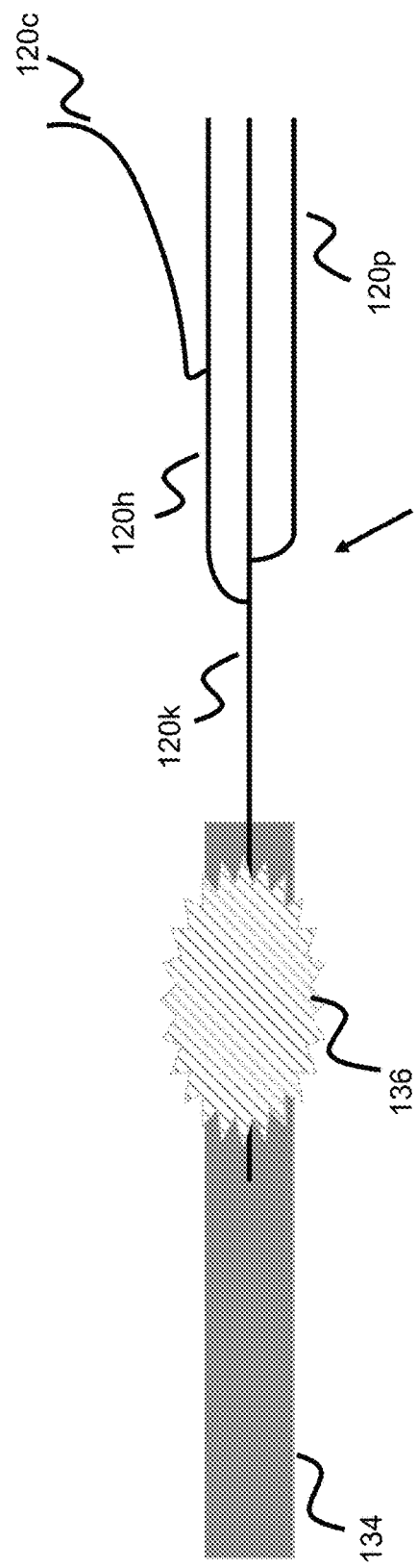
Figure 16
Figure 17

STENT AND STENT CONNECTION INTERFACE

RELATED APPLICATIONS

This application is a continuation of and claims priority to U.S. patent application Ser. No. 16/127,136 filed Sep. 10, 2018 entitled Stent And Stent Connection Interface, which claims benefit of and priority to U.S. Provisional Application Ser. No. 62/563,570 filed Sep. 26, 2017 entitled Stent with a Single End Loop, both of which are hereby incorporated herein by reference in their entireties.

BACKGROUND OF THE INVENTION

Stents are used for various therapeutic purposes within the vasculature, including opening vessels, flow diversion to limit blood flow to a problematic region such as an aneurysm, or as a scaffold to retain other therapeutic material within a target region.

Delivery of stents can be difficult for several reasons. Many stents end in a looped end configuration with a plurality of loops and most stent delivery systems must connect to one or more of these loops to deliver the stents. Stent delivery systems which hold all the loops are difficult since the stents are delivered through relatively small catheters, leaving little room for a delivery design which can grip all the loops. Delivery designs or systems which hold only one loop of the several loops are problematic since the stent is only being partially controlled during delivery. Since stents generally have shape-memory and therefore adopt their expanded shapes quickly once they are released from the delivery catheter, positioning and repositioning stents after delivery is also an issue.

SUMMARY OF THE INVENTION

The following embodiments deal with a stent connection interface which allows multiple stent loops/flares to combine into a common connection, thereby allowing for easier control over a stent during the delivery process.

In one embodiment, a stent connection interface is described. The stent connection interface combines pairs of end stent loops into a common connection.

In one embodiment, a stent is described. The stent has end loops on at least the proximal end of the stent, and the end loops converge into a common connection region by a stent connection interface. The stent connection interface, in turn, connects to a stent delivery mechanism (e.g., a pusher) which is used to control and deliver the stent.

In one embodiment, a stent is described where the stent has a plurality of end loops converging into a common connection region/interface.

In one embodiment, a stent delivery system is described. The delivery system comprises a pusher used to mechanically grasp and position the stent. The stent utilizes a stent connection interface to create a common connection out of a plurality of end loops, the common connection is connected to the pusher where the pusher is used to position the stent.

In one embodiment, a method of creating a stent having a common connection is described. The method comprises taking a stent having a plurality of end loops and connecting a stent connection interface which combines pairs of end loops into a common connection area.

In one embodiment, a mandrel is described which is used to create a stent having a common connection. The mandrel includes a plurality of grooves which accommodate a plurality of stent wires, and the plurality of grooves are patterned such that multiple wires coalesce into a common connection interface.

In one embodiment, a scaffold is described which is used to create a stent having a common connection. The scaffold includes a plurality of channels which accommodate a plurality of stent wires, and the plurality of channels are patterned such that multiple wires coalesce into a common connection interface.

In one embodiment, a stent delivery system is described where the stent delivery system has a pusher which attaches to and detaches from a common connection of a stent.

BRIEF DESCRIPTION OF THE DRAWINGS

These and other aspects, features and advantages of which embodiments of the invention are capable of will be apparent and elucidated from the following description of embodiments of the present invention, in which:

FIG. 14a illustrates a ring configuration of a stent, according to one embodiment.

FIG. 14b illustrates a ring configuration of a stent, according to one embodiment.

FIG. 14c illustrates a common connection interface of a stent, according to one embodiment.

FIGS. 16-18 illustrate a stent delivery system including a pusher, stent connection interface, and stent wires, according to various embodiment.

DESCRIPTION OF EMBODIMENTS

Stents are used for a variety of reasons in the vasculature. For example, propping open vessels to restore blood flow, flow diversion to limit blood flow to a problematic region such as an aneurysm, or as a scaffold to retain other therapeutic material within a target region. Many stents use a plurality of end loops or end flares (e.g., radially flared loops) at either end of the stent; wherein the end loops or flares help anchor the vessel to a particular spot in the vasculature to minimize the chance that the stent will move after deployment. U.S. Pat. Nos. 9,867,725 and 9,439,791 disclose various stent embodiments having end loops or flares, and both patents are hereby incorporated by reference in their entirety.

Figure 1:
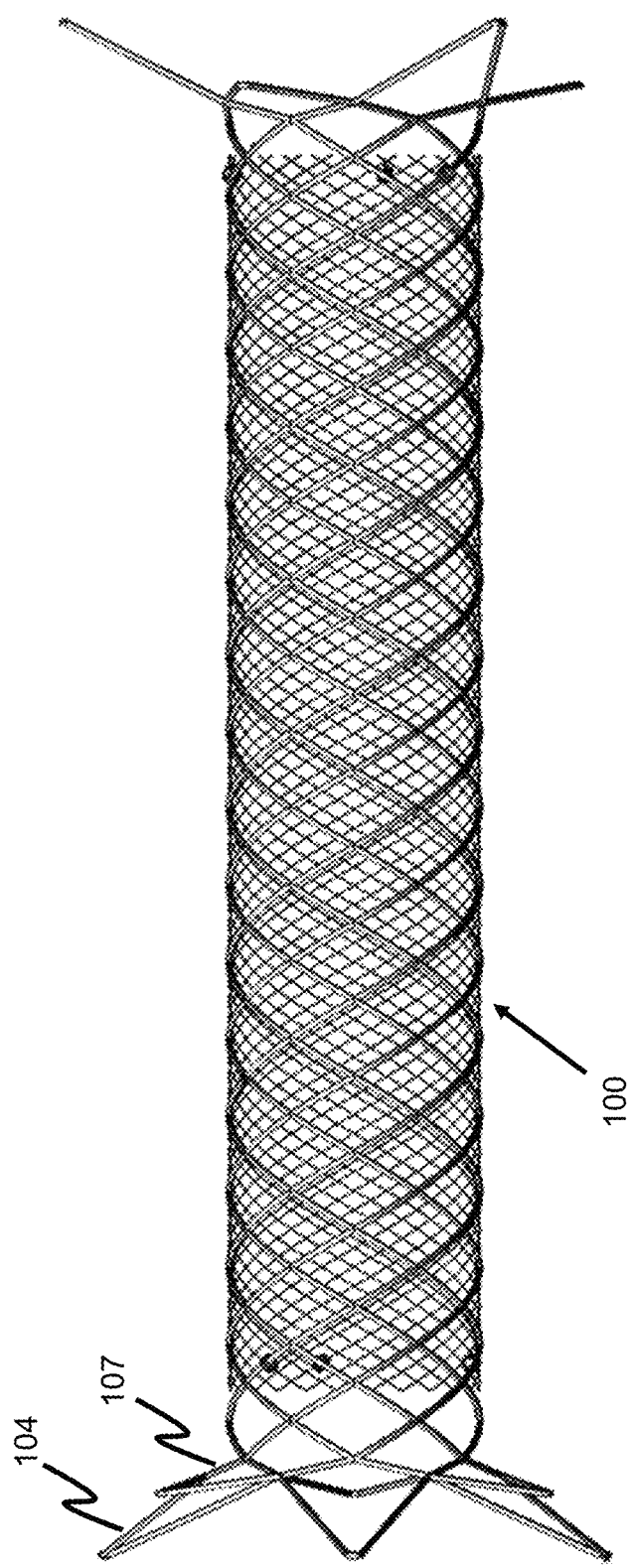
FIG. 1 illustrates a stent with a plurality of end loops or end flares, according to one embodiment.

FIG. 1 shows one example of a stent having a number of end loops at either end of the stent that can radially flare outwards from the main body of the stent in its expanded configuration. These end loops/flares can be created in a number of ways. For example, the stent can have a one-layer or two-layer configuration. In one example, further described in U.S. Pat. No. 9,867,725 9,439,791 which were earlier incorporated by reference, the stent has an inner and outer layer, where the outer layer is comprised of a wire braid wound over a mandrel to impart a number of flares or loops which protrude from the stent at both ends. A stent can also utilize a single layer comprised of one or more wires wound into a particular pattern, where each end of the stent includes a number of flares or loops. Such a stent is described in the patents referenced and incorporated by reference above.

Other stents can utilize a dual or two-layer configuration where the outer layer is formed of a series of wire pairs where each wire pair forms a flare or loop at the ends of the stent. One such stent utilizing this configuration is described in US Published Application No. 2017/0079812, which is hereby incorporated by reference in its entirety.

Stent 100 shown in FIG. 1 has a plurality of loops or flares at each end of the stent that extend both longitudinally and radially outward from the main body of the stent. Some of the loops are shorter 107 and some are longer 104, as shown best in FIG. 2. These short and long loops are placed next to each other in an alternating pattern so that one long loop is next to one short loop, which in turn is next to a long loop, etc. Various loop combinations are possible, for instance, each end of the stent can have 6 loops (comprised of 3 long loops and 3 short loops, in the pattern defined earlier where the loops alternate), or 8 loops (comprised of 4 short loops and 4 long loops, in the pattern defined earlier where the loops alternate), or more or fewer loops.

Figure 2:
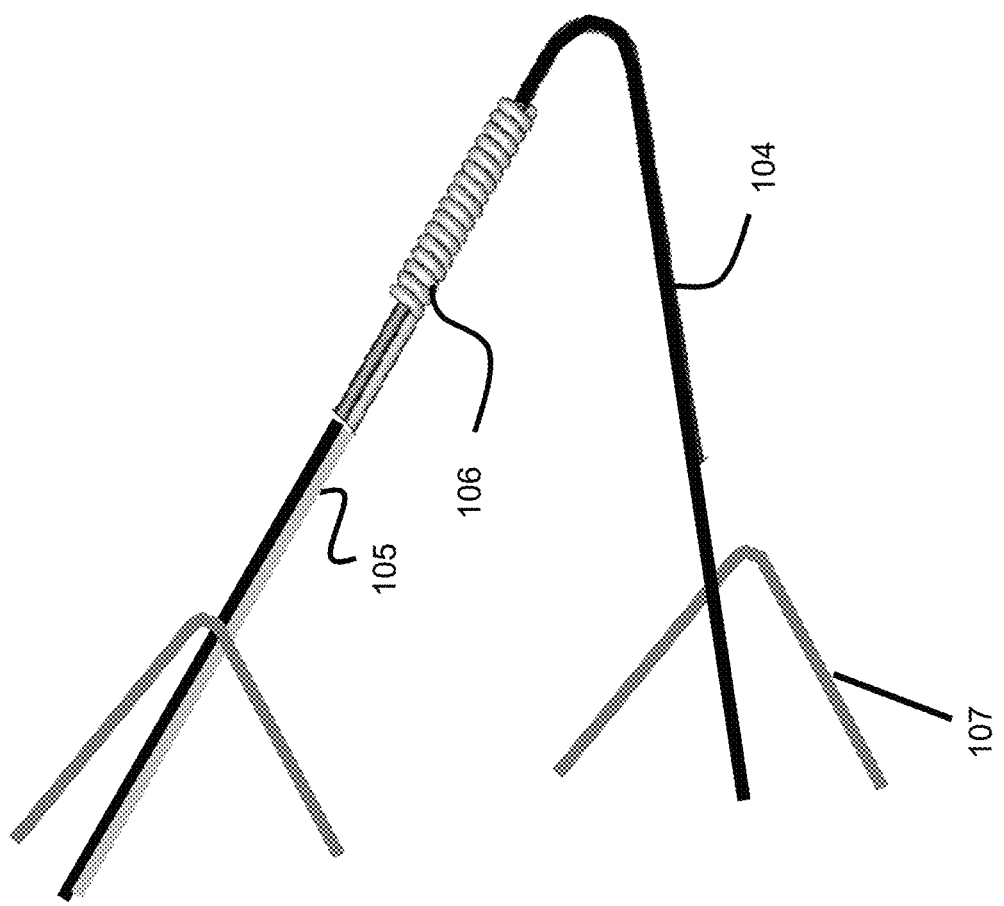
FIG. 2 illustrates an end loop or end flare of a stent, according to one embodiment.

In one embodiment, shown in FIG. 2, the long flares or loops 104 may utilize a tantalum wire 105 for radiopacity, where the tantalum wire is wound between the inner and the outer layer of a dual layer stent to aid in binding the layers together. This wire 05 terminates with a coil 106 on one or more of the long loops 104. These loops or flares serve various purposes, including helping to anchor the stent in the vasculature to prevent movement after the stent is deployed as well as helping to prop the stent open as it is deployed from the delivery catheter. Though long and short loops are not necessary (e.g., in other embodiments the stent can have a series of equally sized end loops), the presence of long and short loops offers some advantages in terms of distributing friction circumferentially though/around a radial region of a delivery catheter when the stent is being deployed through the delivery catheter.

Delivering a stent with these end loops can be difficult since each loop represents a different and separate grasping interface. Designing a delivery system that can grasp all of the loops can be challenging since each loop represents a different contact interface spread circumferentially and peripherally around the stent. Meanwhile, utilizing a delivery system that mechanically grasps only one of the several loops can limit control of the stent during the delivery process since only a small portion of the stent is being physically controlled. The following embodiments seek to address this problem by utilizing a connection interface which connects to these end loops or flares to create a common connection region which is then connected to a delivery system to deliver the stent.

Figure 3:
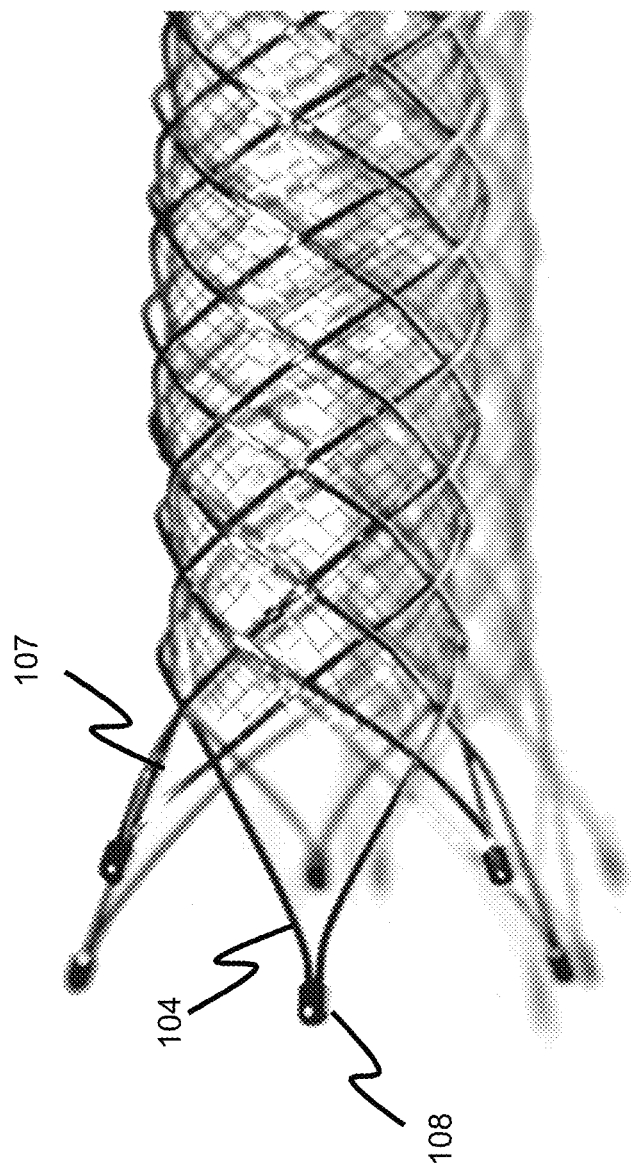
FIG. 3 illustrates a stent with bands use to bind wires which form a plurality of end loops or flares, according to one embodiment.

Stent 100 is preferably comprised of metallic wire, meaning the stent itself as well as the end loops on either end of the stent are comprised of metallic wire such as nitinol—although other variations could involve the stent being comprised of different materials such as polymers. Alternative stent construction configurations could also utilize DFT or drawn-filled tubing, which is typically comprised of a radiopaque core (e.g. platinum, tantalum, gold, silver, titanium or tungsten wire/element) surrounded by a thin metallic (e.g. nitinol) jacket—DFT offers the advantage of radiopacity, so a stent comprised of DFT where the DFT comprises some or all of the metallic mesh will have heightened radiopaque imaging properties and will not necessarily need additional radiopaque wires/coils to aid in visualization. In one embodiment, the stent is a dual layer stent having an inner layer and an outer layer, where the flares at both ends of the stent are located on the outer layer. The outer layer, which includes long flares 104 and short flares 107, is preferably made of a multiple wire braid where pairs of wires converge to create the triangular flares best shown in FIG. 2. In other words, two separate wires converge and then connect at or near the end or tip of the flare/loop to form the flare/loop. For instance, a stent comprising an outer layer having four short flares 107 and four long flares 104 is preferably made of a sixteen-wire braid total forming the eight flares (comprised of four long flares 104 and four short flares 107). The wire pairs are normally welded together or alternatively affixed together by a mechanical cap 108 that is welded to the two wire ends of the short flares/loops 107 and long flares/loops 104 at either end of the stent—as shown in FIG. 3, and discussed in more detail in U.S. Pub. No. 2017/0079812, the contents of which are incorporated by reference.

Figure 4:
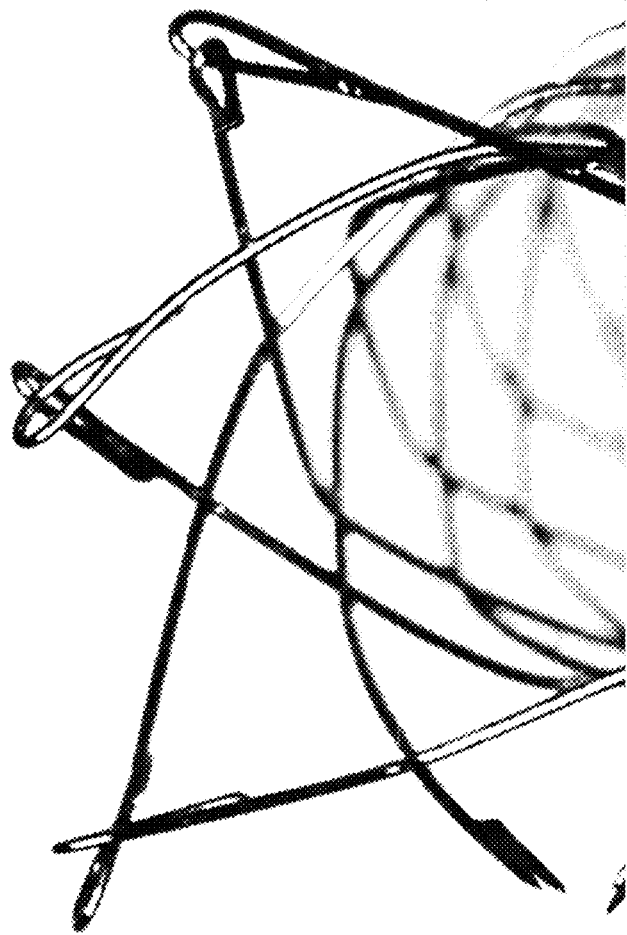
FIG. 4 illustrates a stent utilizing a fish-hook configuration to bind wire pairs, according to one embodiment.

Alternatively, each wire can be fish-hooked or bent back at the ends, and then passed through the other wire as shown in FIG. 4 to create the mechanical connection. A first wire is fish-hooked or bent back and welded to create a circular loop, the second wire is then tracked through this loop and bent back and welded at a proximal location along the second wire to create the connection between the two wires. These stent end concepts—including the capped end configuration and the fish-hooked end configuration—are discussed in more detail in US Published Application No. 2017/0079812, which was earlier incorporated by reference in its entirety.

To create the stent winding pattern and shape, a mandrel is used where the wires comprising the stent are wound over the mandrel to create the stent shape. The stent is often then heat set over the mandrel to impart a shape memory into the stent, such that the stent will adopt its expanded, shape memory configuration when deployed from a delivery catheter. The following embodiments utilize a mandrel with a number of grooves to accommodate the stent wires. The grooves are arranged in a particular pattern such that the groove pattern converges into a common connection region such that the stent flares converge into a common connection region which can then be held by an implant pusher/delivery system. In this way, a stent is created whereby a plurality of flares merge to a common connection region to make stent delivery easier.

Figure 5:
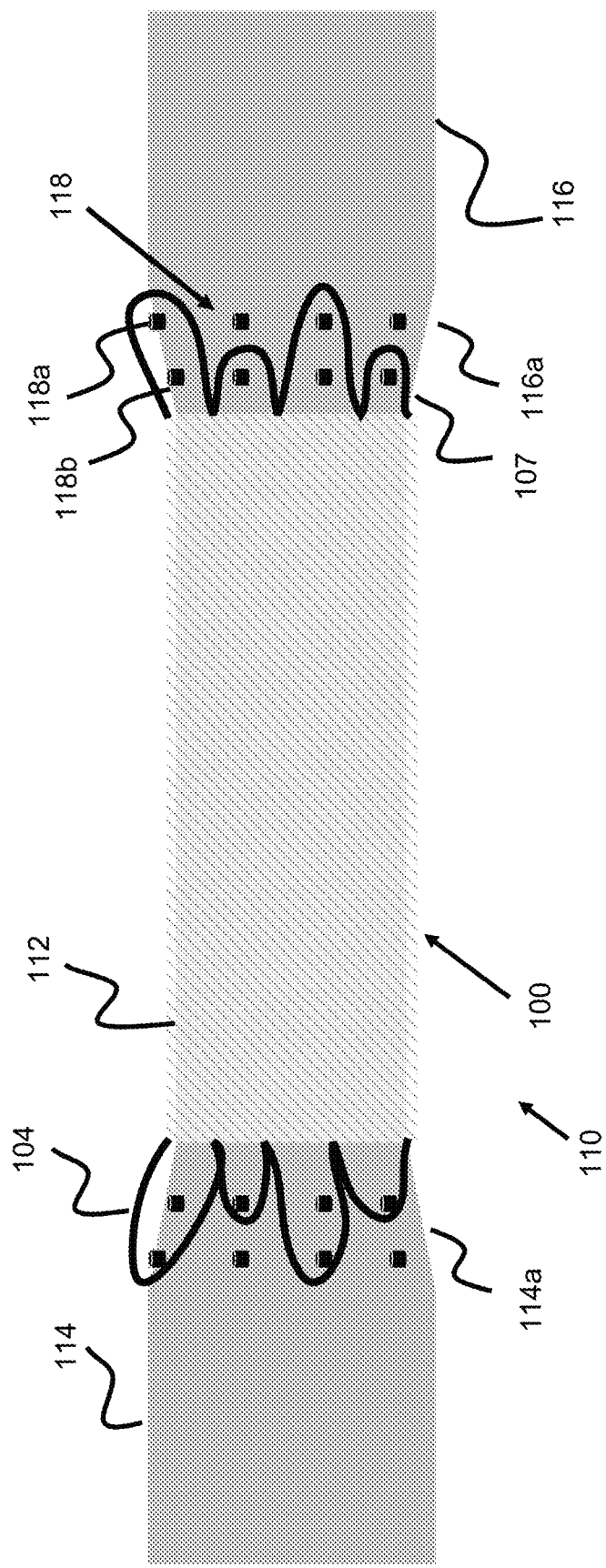
FIG. 5 illustrates a mandrel used to wind a stent, according to one embodiment.

Since the flares 104, 107 are generally enlarged and protrude relative to the stent 100 (as shown in FIG. 1), the mandrel used to wind the stent may also use enlarged regions used to create these flared sections. FIG. 5 shows such a cylindrical mandrel 110 used to wind a stent 100. Mandrel 110 comprises a smaller diameter middle section 112, tapered sections 114a and 116a which are used to create the flares and abut smaller middle section 112, and enlarged regions 114 and 116 abutting the tapered sections. A first tapered section 114a abuts enlarged end region 114 and a second tapered section 116a abuts enlarged end region 116. Middle section 112 has the smallest diameter, enlarged regions 114 and 116 have the largest diameter, and tapered regions 114a and 116a have a tapered diameter such that the tapered region tapers (e.g., linearly) between the smaller and larger diameter.

The tapered sections 114a and 116a contain a number of pins 118 protruding radially and perpendicularly outwardly from the surface. The wires forming the stent/stent layer are wound around the pins to create the loop shapes. Where the stent has a series of short loops 107 and long loops 104, the pin locations are radially spread out such that some pins 118a are radially further out, and some pins 118b are radially closer. Pins 118a that are radially further out are used to wind the long loops 104 and pins 118b that are radially closer are used to wind the short loops 107. In other embodiments where the flares or loops are all of a similar size, pins along a similar radial location (e.g., only pins 118b or only pins 118a) are used to wind the various stent loops—alternatively, in such embodiments, the mandrel is configured only with one set of pins (e.g., either pins 118b or pins 118a) so that the stent is solely wound around a set of similarly-placed radial pins to create a stent with equally sized end loops or end flares.

The pins are used to impart the flared or loop shapes in the following manner. In one embodiment, the one or more wires comprising the relevant stent/stent layer would be wound around the pins to impart the particular flared loop shape, such that the wire is bent around the pin and wound back into the stent to impart the flared or looped shape. One example where this embodiment can be used is where the relevant stent or stent layer incorporating the flares is made of one wire, such that the one wire is continuously woven back and forth and around the pins. Another example is where the relevant stent or stent layer is comprised of multiple wires but each wire is used to wind a loop or flare at each end of the stent, where one wire is used to create one loop at one end of the stent and wound back to create another loop at the other end of the stent, a second wire is used to create a second loop at one end of the stent and a second loop at the other end of the stent—in this manner, an stent with 8 loops at either end (8 loops at one end, and 8 loops at the other end) would comprise 8 wires, or one for each loop. In some embodiments, the flared loops are formed of wire pairs, and the loops can be made in different ways. For instance, the wire pairs are welded or capped at their ends beyond the pin location. Alternatively, one of the wires would be pulled backwards proximal of the pin and then welded or affixed to the other wire comprising the wire pair. With these embodiments, the loops are formed from two distinct wires coming together and then affixed to each other to create the loop or flared shape.

In order to create a common connection point or common connection region from the plurality of end flares or loops at one end of the stent, one of the mandrel sections would contain a series of channels or grooves to accommodate the stent wires, where the wires would be placed into a particular pattern etched or cut into the mandrel to funnel the plurality of wires into a pattern that ends in a common connection point. These channels or grooves could be created in a number of ways—for instance, laser-cutting, etching, and mechanical cutting. Note, only one of the mandrel sections would need the groove pattern and not both since the groove pattern is used only on one end of the stent since only one end of the stent (e.g., the proximal end that is meant to be connected to the delivery pusher/delivery system) needs the common connection interface.

Figure 6:
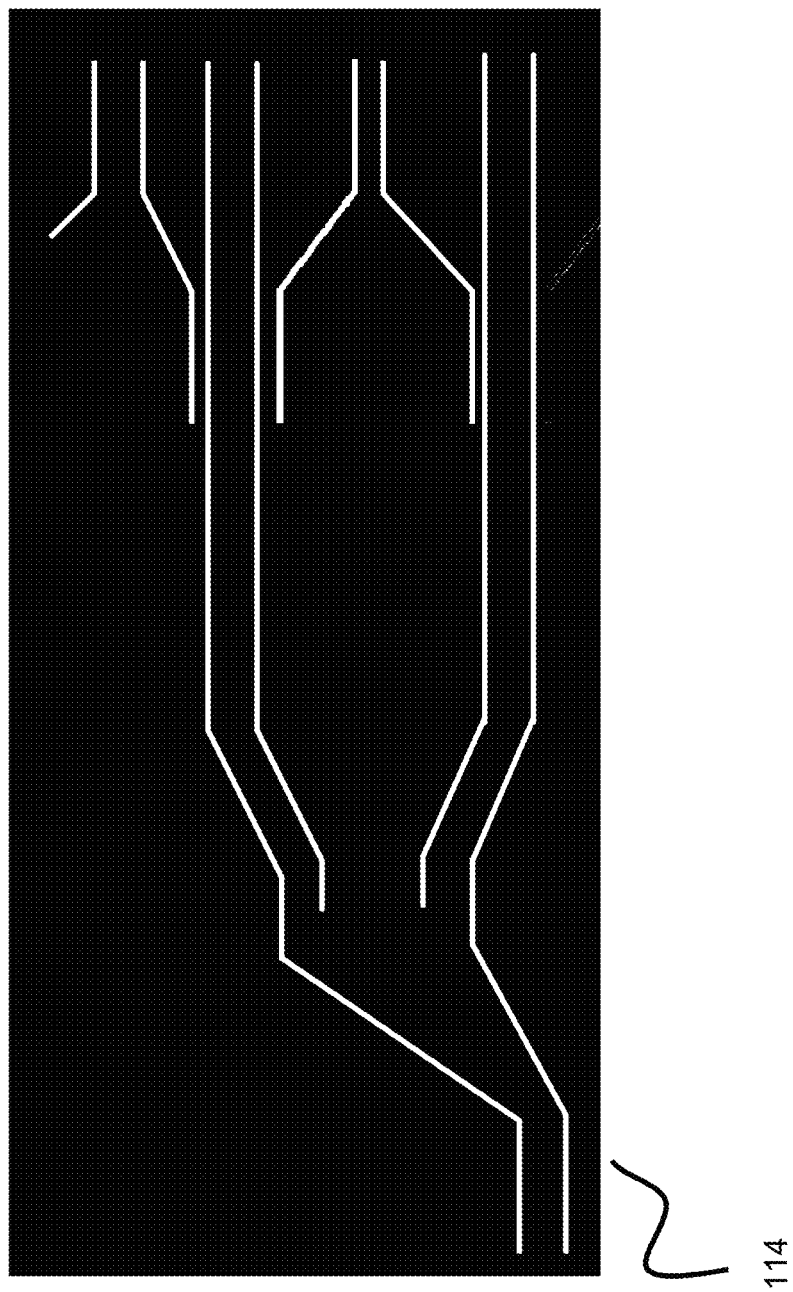
FIGS. 6, 7, 8, 9, 10, and 11 illustrate a groove configuration on a mandrel, according to various embodiments.
Figure 7:
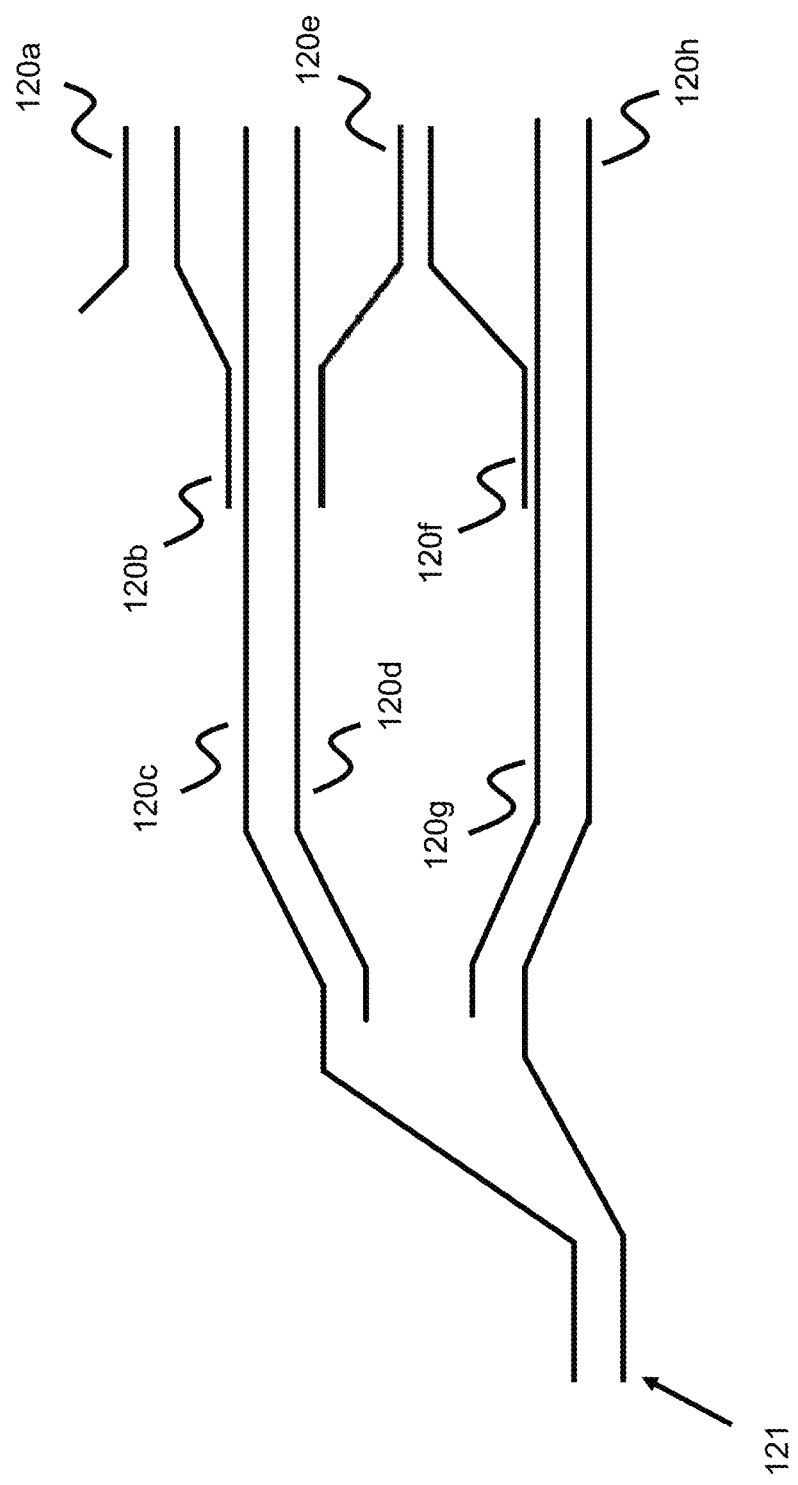

This mandrel concept is shown in FIG. 6, where enlarged mandrel section 114 (which sits past tapered section 114a used to wind the stent flares/loops) has a number of grooves etched, laser cut, or otherwise cut or imparted onto the surface. This groove pattern is shown in more detail in FIG. 7. Each groove/groove element 120a-120h can be thought of as an indented receiving surface which receives or accommodates the wire. The shorter, or less lengthy groove lines (e.g. groove elements 120a, 120b, 120d-120g), represent wires which terminate prior to the (left) ending or common connection point/region 121 (see FIG. 7), the idea being several wires will gradually converge into each other before then converting to a common connection end region 121. Note, the next portion of the description will expound on this groove/wire concept, however since the wires are placed into the noted groove elements, the figure elements can interchangeably be used to describe either the groove element or the wire which would sit within the groove element; as such, the description can vary between using the figure elements to describe either the groove element or the wire which sits in the groove element.

Figure 8:
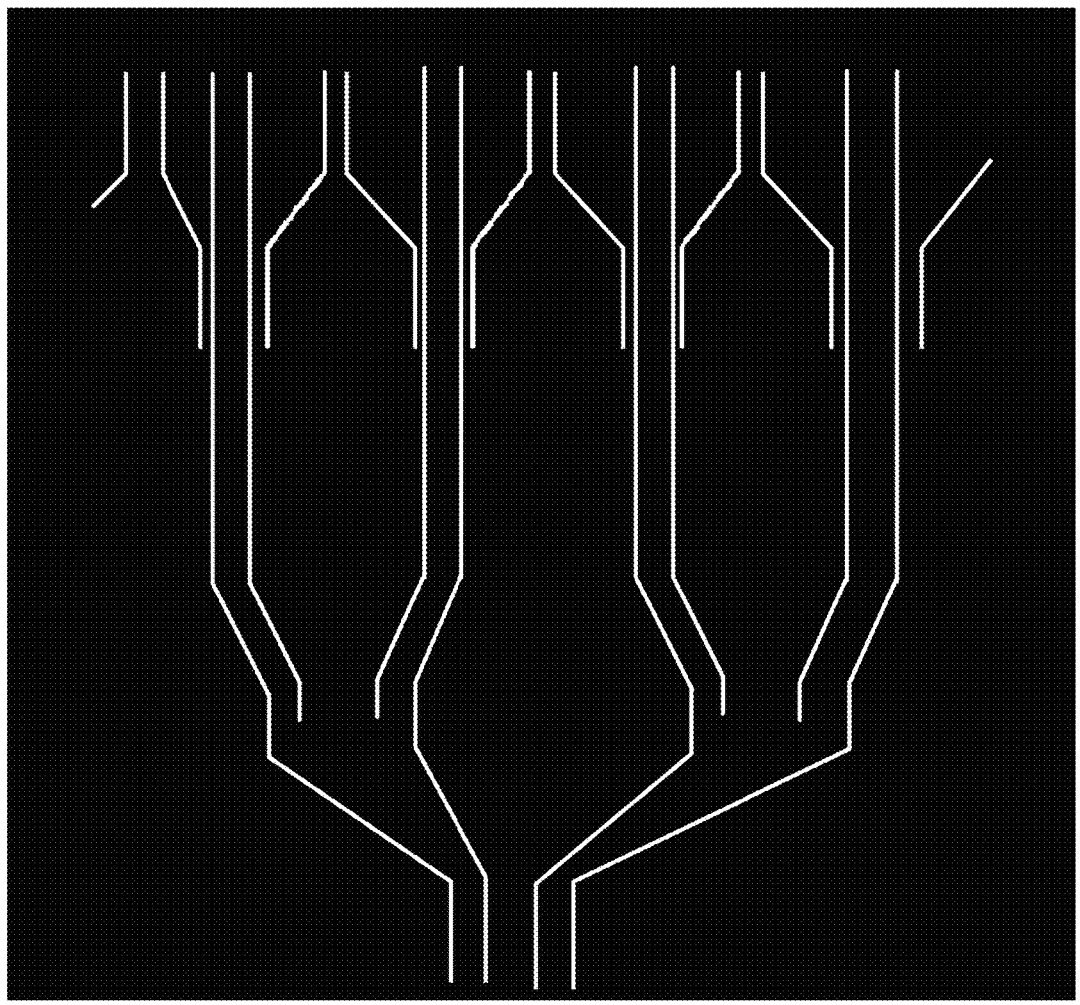

FIG. 8 shows a flattened view of the groove interface over the enlarged region 114 (and/or 116) of the mandrel, and can be thought of as a complete-view representation of the cylindrical mandrel pattern around the enlarged region. In other words the pattern in FIG. 8 would be etched or cut around the circular enlarged region of the mandrel and FIG. 8 shows what this pattern would look over the entire cylindrical structure if a single cut was made in an axial direction across enlarged cylindrical mandrel region 114 and the mandrel was then unfurled along this region to create a rectangular representation of the mandrel. FIG. 8 shows 16 grooves, so this pattern would allow 16 wires to coalesce down to 4 wires, where the 4 wires are nested close to each other to create a common connection interface.

Figure 9:
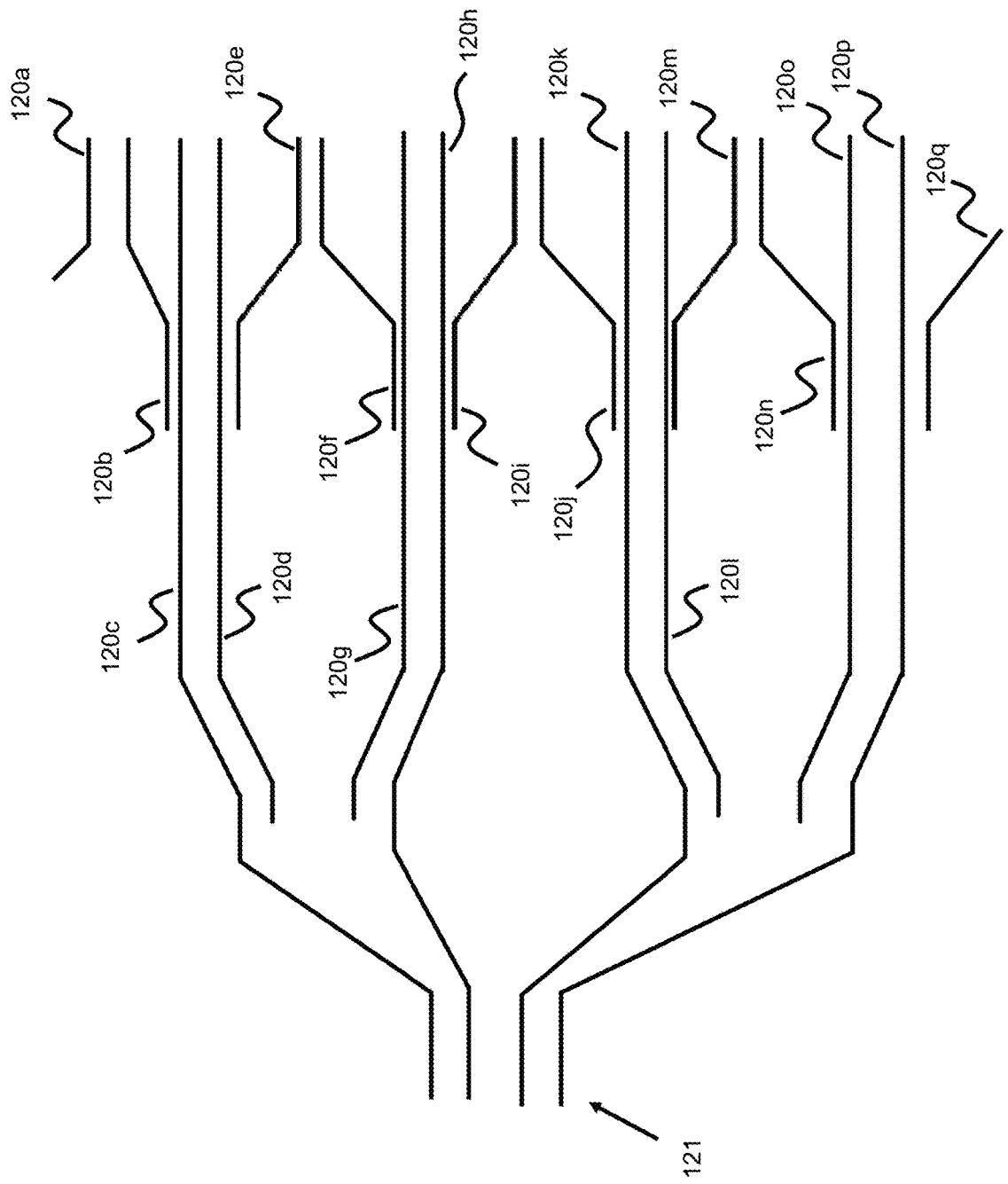

FIG. 9 shows the groove interface in more detail, where the respective grooves are labelled, and common connection region 121 is identified. Since the groove pattern would in fact be cylindrical since the pattern is placed over the cylindrical mandrel, groove 120a and 120q are complementary in the sense that a wire placed in groove 120a would sync up or align with a wire placed in groove 120q such that the wires would be welded to each other and thereby connect since they would align with each other when placed over the circular mandrel. Again, FIGS. 8-9 represent the entire circular mandrel so grooves 120a-120h are shown already in FIGS. 6-7 and the "new" grooves 120i-120q represent the grooves that sit along the rest of the cylindrical face of the mandrel.

Figure 10:
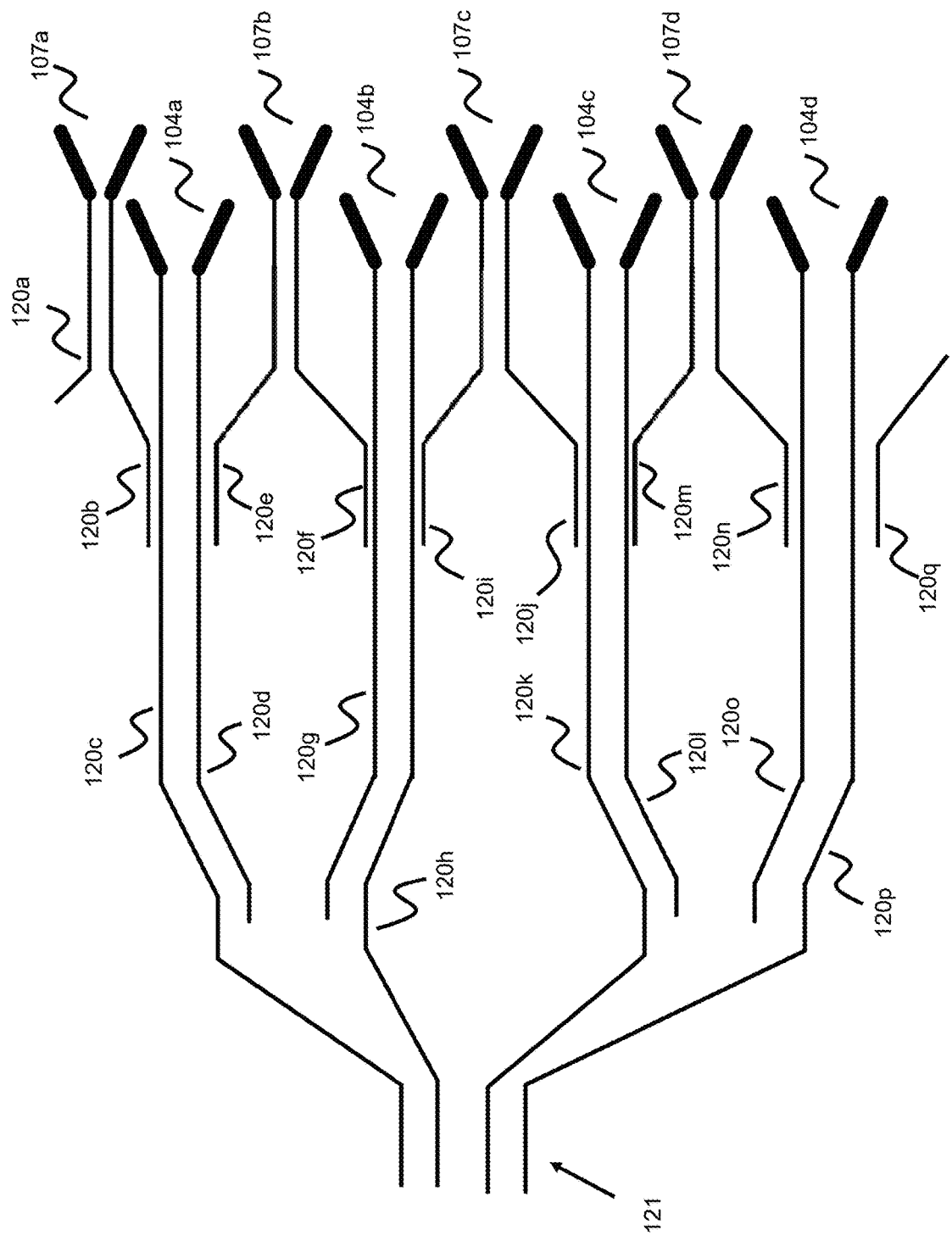

FIG. 10 shows how the various short flares (107a-107d) and long flares (104a-104d, which it should be noted sit "closer" to the whole groove interface thus indicating the protruding nature of these lengthier flares) interact within the larger groove pattern. Each flare is formed of two wires, each wire within the pair is then placed within the groove on the mandrel, where some grooves (120c, 120h, 120k, 120p) are longer and meet in a common location to create a common connection interface 121—and the other grooves are shorter and terminate prior to common connection region 121.

In the groove pattern shown in FIGS. 8-10, there are 16 grooves representing 16 wires which would normally form 8 flares (4 short flares 107a-107d and 4 long flares 104a-104d). Eight of these grooves (120b, 120e, 120f, 120i, 120j, 120m, 120n, and 120a/120q which together form one element which terminates at the same location as the other grooves in the series—as discussed above in how these grooves are actually over a cylindrical mandrel and therefore the grooves accommodate a common wire which is attached to the wire or groove 120p) terminate at a common location and are considered the "shortest" grooves in terms of length. Four of these grooves (120d, 120g, 120l, 120o) terminate at a common location are considered "intermediate" grooves which are longer than the shortest grooves but do not span all the way to the common connection interface 121. Four of these grooves (120c, 120h, 120k, 120p) are the "longest" grooves which combine to create the common connection interface 121 which connects to the delivery pusher. The 16 initial wires forming the 8 "flares" or "loops" thus merge down to 4 wires forming a common connection interface 121.

In an alternate embodiment, the 4 wires 120c, 120h, 120k, 120p forming common connection region 121 can further be condensed. For instance, wire 120c and wire 120h can be attached to each other, and wires 120k and 120p can also be attached to each other, creating a common connection region comprising two wires. These two wires can then optionally be attached to each other at another location to produce a common connection region comprising one more. Therefore, although FIG. 10 shows a common connection region 121 comprising four wires, it is possible to create a common connection region comprising even fewer wires. This concept will be explained in more detail later in the specification, when the mechanical connection between the common connection region 121 and the delivery pusher is discussed in further detail.

After the wires are placed into these grooves, the portion of the wires sitting beyond the grooves are trimmed since different wires will have different lengths corresponding to the respective groove lengths. For example, the stent wire sitting in groove 120b would be shorter than the stent wire sitting within groove 120c since groove 120c is longer, therefore the portion of the stent wire sitting beyond the end of the groove 120b will be trimmed. After this trimming step is taken, the stent itself can be heat set to impart a shape memory and then the wires are removed from the mandrel. The wires still have to be removed from the grooves and attached to each other at their respective groove locations, therefore, for example, wire 120b is attached along longer wire 120c. This attachment can be done in a number of ways—for instance, via welding, adhesive, crimp, or solder. Alternatively, a mechanical connection interface such as an overlying cylindrical tube which has an internal diameter large enough to contain the various wires can be used to bind two or more wires. In an alternative arrangement, the heat setting step to impart the shape memory can be taken after the various wires are attached to each other to create the "step-down" pattern culminating in common connection region 121.

With the mandrel configuration shown in FIG. 5 and described earlier, the grooves sit on the larger cylindrical mandrel region 114 where the wires that form the stent flares are drawn over the enlarged mandrel face into grooves on mandrel region 114. In order to create a common connection interface, all or part of the mandrel can, in one example, have a smaller diameter section on the terminal end of the larger region 114 so that the end wires taper down to a smaller diameter and can be heat-set into this smaller diameter shape. Alternatively, a mandrel configuration like that shown in FIG. 12 can be used where the pins 118 used to wind the end loops or flares of the stent are on an enlarged region 122a and 122b of the mandrel. Radially smaller sections 124a and 124b are adjacent these enlarged regions and the groove pattern interface sits on either one of these regions (in practicality, as described earlier, only one end of the mandrel needs the grooves since the common connection region 121 is only needed on one end of the stent which connects to the delivery pusher). The advantage of this configuration (where the groove pattern 120a-120q shown in FIG. 10 is imparted on the smaller mandrel section 124a/124b) is that the wire sections connected to the end loops will naturally assume a radially smaller configuration, making it so that the common connection interface formed of the four "grooves" 120c, 120h, 120k, 120p will be located closely together, especially after the stent is heat set over the mandrel.

Figure 12:
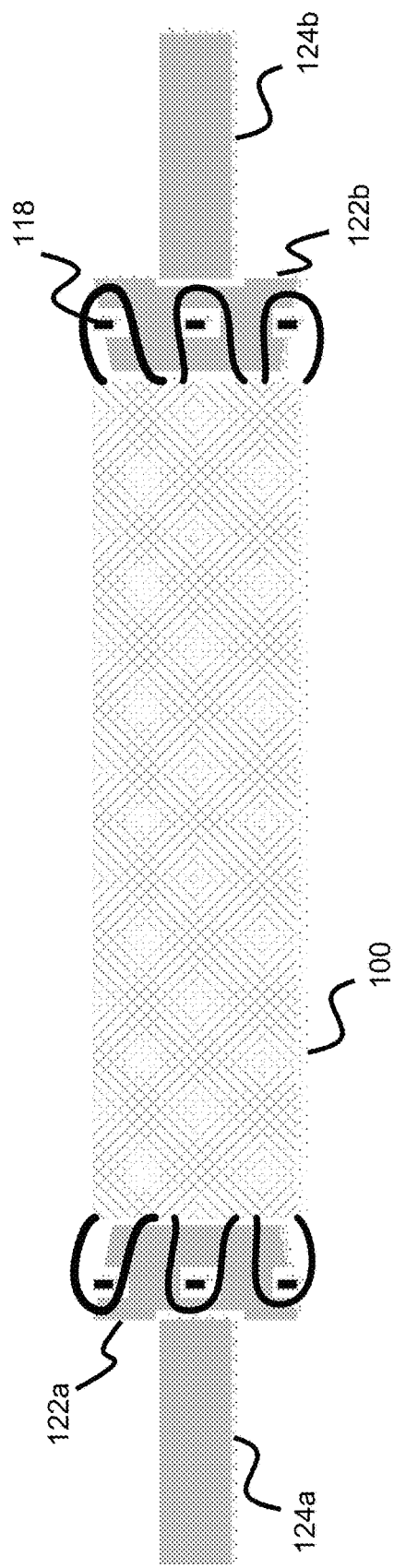
FIG. 12 illustrate a mandrel used to wind a stent, according to one embodiment.
Figure 13:
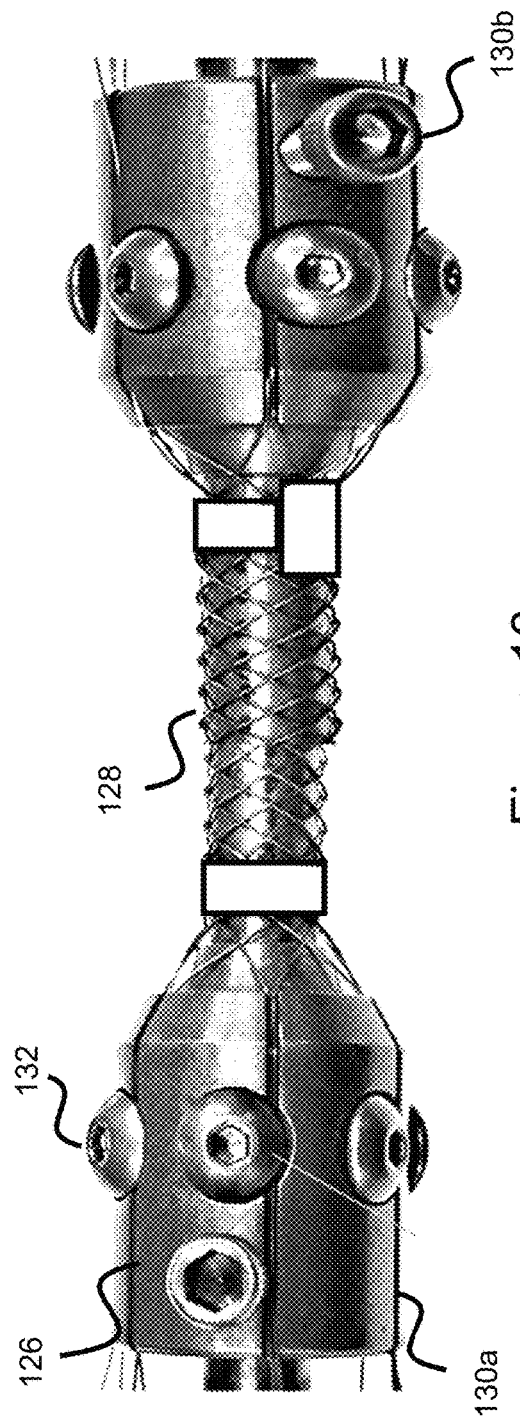
FIG. 13 illustrates a mandrel used to wind a stent, according to one embodiment.

FIG. 13 shows an alternative mandrel configuration where a pin-less interface is used to create the stent flares/loops. A smaller radial region 128 sits in the middle of the mandrel and is used to wind the majority of the stent. A larger region 130a, 130b at both ends helps create the loop or flare, and both regions 130a and 130b contain a number of channels 126 that the pairs of wires forming the loops or flares are placed into—in other words, each channel 126 accommodates two wires. Since the flares are created by the wire pairs being placed into the channels, a pin is not needed to create the loops or flares, rather the loops/flares are created by the wire pairs being pulled into the channels which sit on the enlarged radial region 130a/130b. A number of screws 132 are optionally placed radially around the enlarged regions 130a, 130b where the circular region housing the screws overlap part of the channels 126b such that when the screws are tightened, they overlie the wires in the channels thus ensuring the wires do not fall out of the channels. Though not shown, the groove configuration shown in FIG. 10 would be located along the enlarged region of the mandrel 130a near where the wire pairs first combine into a channel 126. Therefore, the channels would branch off into the groove configuration of FIG. 10 somewhere near the initial region where the wire pairs combine into each channel. In another embodiment, a first enlarged region would house the initial channel 126 where the enlarged region is used to create the enlarged flares or loops; and a smaller radially recessed region (similar to regions 124a/124b or FIG. 12) then utilizes the groove configuration of FIG. 10 to create the common connection interface from the plurality of wires/wire pairs which form one end of the stent.

Though the mandrels have primarily been described as having grooves or channels to accommodate the wires, alternative configurations can utilize a series of wire holding elements placed over the mandrel where the holders/holding elements form the grooves/channels to accommodate the wires. In this way, a guiding interface is formed to guide the wires, however no cuts or recesses on the mandrel would be necessary, rather the guide channels would simply be built over the particular section of the mandrel. In one embodiment, the guiding interface is a scaffold that is placed over the mandrel and the mandrel can contains recesses, where a removable pin or retention element is used to temporarily secure the scaffold to the recesses of the mandrel. In this way, the overlying guide interface can be temporarily affixed over the mandrel to guide the stent wires into a pattern like the pattern shown in FIGS. 8-10, to culminate into a common connection region 121.

Alternatively, a scaffolding interface can connect to the loops of the stent where the scaffolding interface has the guide holders described above to guide the particular wires in a particular way, where the wires sit within the guide holders. With this embodiment, there would be no need for a scaffold or guiding interface to be "built over" the mandrel, rather the mandrel section would terminate with the part of the mandrel accommodating the loops. The scaffold interface would then be placed adjacent to the end loops, where the scaffold interface is comprised of a series of holders forming a pattern corresponding to the groove interface embodiments shown in FIGS. 8-10. The scaffolding interface can still adopt a generally circular profile to emulate the circular mandrel surface, however the scaffold interface would basically contain a series of wire holding elements which together adopt a circular profile (to correspond to the cylindrical shape of the stent and the circular-type shape of the stent ends and how the stent loops proceed circularly around the end of the stent) where the holding elements contain the wires of the stent. In this manner, a wire guide mechanism can be implemented independent of the stent mandrel.

Alternatively still, the scaffolding interface can adopt a mandrel configuration but not actually be part of the physical mandrel itself which is used to wind the stent. The scaffolding interface would be a circular element with a wire-holding pattern cut into the surface (as grooves) or built over the interface (as protruding holding elements). In this embodiment, the scaffolding interface is best thought of as a detached, movable mandrel which can be placed adjacent to the end stent loops/flares, such that the stent wires can then be drawn through the wire guides of the movable mandrel.

In another embodiment, the entire groove pattern illustratively shown in FIGS. 8-10 is a prefabricated entity which is either comprised of wires or a laser cut sheet, such that the wires or retained elements of the laser cut sheet are patterned similar to the groove pattern of FIGS. 8-10. The entire prefabricated entity is the attached to the end loops of the stent through adhesives, mechanical means such as ties, or welding. In this way, the stent with its end loops is a first separate structure, the second attachable prefabricated entity which reduces the stent flare pattern to a common connection interface 121 is a second separate structure, and the two structures are attached together to create a stent which includes a common connection region 121.

Figure 11:
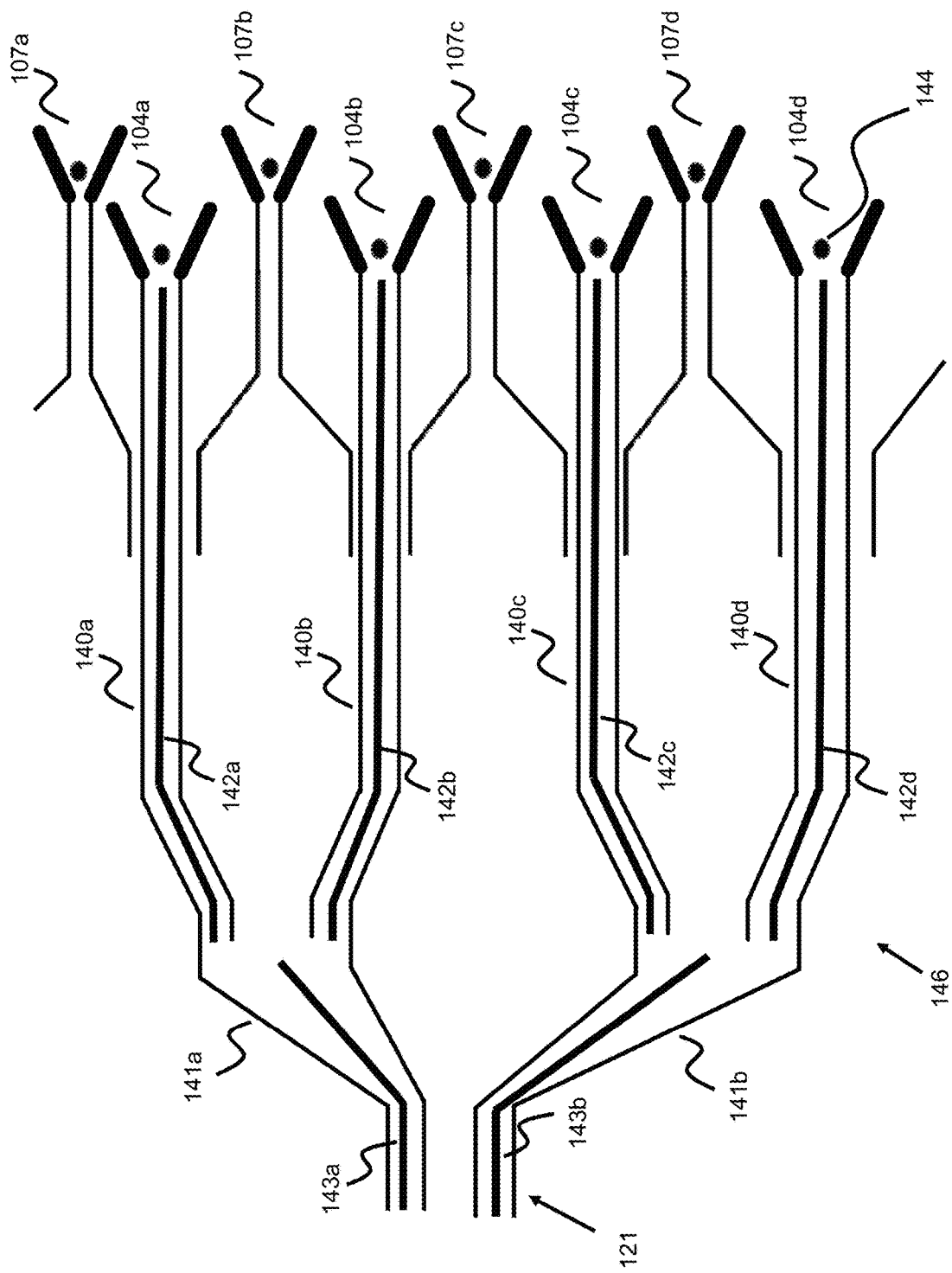

Some of the embodiments presented herein utilize a separate wire structure or laser-cut structure which connects to the stent flare region to create a common connection interface. For example, a scaffold or frame structure which connects to the stent flares to guide the stent wires in a particular direction. FIG. 11 shows such an embodiment, where a scaffold or frame element connects to the stent flares (both short flares 107a-107d and long flares 104a-104d). The frame element comprises a series of channel elements 140a-140d, where separate wire elements sit within the channel elements such that the wires condense down to a smaller common connection interface 121. The frame element can be thought of as a fixture connected to the stent/stent flares, and a series of pins 144 can be used over the flares to bind the flares to the connecting frame fixture. In FIG. 12, each long flare 104a-104d is connected to a corresponding frame channel element 140a-140d. The frame channel element 140a-104d accommodates a wire 142a-142d. The end part of the frame channel condenses down to a smaller element 141a, 141b (whereby elements 140a and 140b meld into element 141a and elements 140c and 140d meld into element 141b, where frame elements 141a and 141b hold a separate wire 1413a and 143b. Wire 142a and 142b are connected at their converging section (e.g. through welding), and then are connected to wire 143a to form one connected wire. Similarly, wires 142c and 142d are connected at their converging section and then connected to wire 143b to form one connected wire. Wires 140a-140d are further connected to the corresponding flare element 104a-104d. In this way, each long flare 104a-104d is connected, such that four long flares 104a-104d converge down into a two-wire common connection interface 121. In one embodiment, wires 143a and 143b can then be connected to form a one wire common connection interface 121. While in the embodiment of FIG. 10 the wires of the stent loops are then wound into a particular pattern, here the stent loops (e.g. longer stent flares 104a-104d) are used as a connection mechanism to a frame, where the frame provides a holding interface for wires which in turn connect to the longer stent flares 104a-104d).

The following embodiments utilize an alternative configuration to link the stent flares together, these embodiments utilize using wires to link the stent flares together in a ring like pattern and then connecting a common connection interface to this ring-like pattern. Since the flares form a generally circular pattern around the end of the stent, as shown in FIGS. 1-4, the flares can in turn be connected together with wires to connect the flares in a circular pattern where one or more wires connect between the flares to form a circular connection pattern. A common connection interface 121 connects to the ring-type shape, where the common connection interface can be a wire or tube. In one example, the common connection interface is a wire that connects to solely one of the stent flares—in this way, all the stent flares are connected together in a ring-like pattern, while a single common connection interface is then connected to only one of the stent flares. This configuration is generally shown in FIG. 14a where the stent loops 104a, 104b, 107a (just three loops are illustratively shown for ease) connect to a circular ring like pattern 150. Note, in the embodiment shown separate wire elements 154 connect between the ring and the stent flares, however as described above, the stent loops can directly connect to each other to form the ring pattern 150 as well.

In another embodiment, half of the stent flares are connected with a first wire or series of wires and half of the remaining stent flares are connected with a second wire or series of wires. This can be thought of as a first linked "half-ring" and a second linked "half-ring". Each half-ring will have its own connected common connection interface, therefore a two-wire common connection interface is created, where a first wire is connected to the first half-ring, and a second wire is connected to the second half-ring.

In another embodiment, a braid of wires is used to connect the various flares together and this braid of wires forms a generally circular pattern connecting the various stent loops/flares together, where this wire braid forms the ring-type shape. In another embodiment, the short flares are all connected by one or more wires and the long flares are separately connected by one or more wires such that both the short flares and long flares are separately combined by two separate rings. Another binding structure, such as a wire, then connects the two rings.

In another embodiment, a circular pattern is utilized to connect the various flares, however the circular pattern is tapered. This configuration is shown in FIG. 14b where a tapered ring pattern 152 is connected to the stent flares 104a, 107a, 104b. Note, in the figure separate wire elements 154 connect between the ring 152 and the stent flares, however as described above, the stent loops can directly connect to each other to form the tapered ring pattern 152 as well. One advantage to this tapered ring design is that the common connection interface can project from the part of the ring that projects the most (e.g., the bottom left part of the ring in FIG. 14b) to create a connection point that diverges from the rest of the stent. This type of configuration is also shown in FIG. 15a. The tapered ring configuration can also be produced utilizing only two stent flares, where a recessed portion of the ring (e.g. the top ring portion of FIGS. 14b/15a) is connected to the first flare, and a projecting portion of the ring (e.g., the bottom ring portion of FIGS. 14b/15a) is connected to the second flare, and a lengthier wire spans from the second flare to the projecting portion of the ring as highlighted in FIG. 14b.

Alternatively, the common connection interface 121 can comprise a number of wires 154 which directly connect to the stent flares and converge to a common connection point—as shown in FIG. 14c.

Figure 14D:
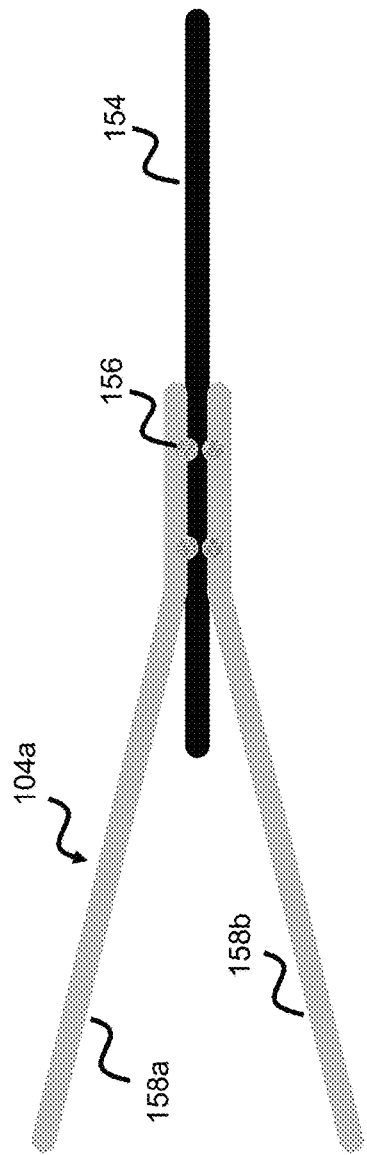
FIGS. 14d-14e illustrate a connection point between a stent loop and a wire element, according to various embodiments.
Figure 15A:
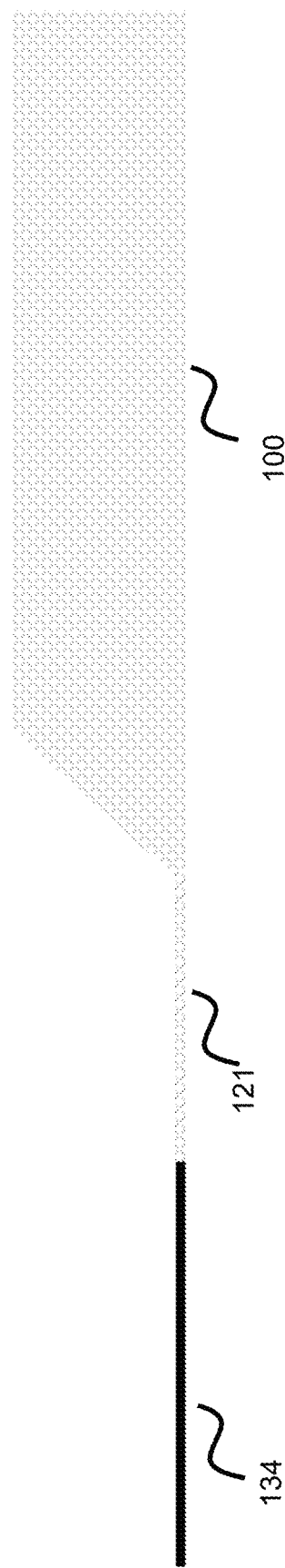
FIG. 15a illustrates a stent delivery system, according to one embodiment.

FIGS. 14a-14c and the description above generally touch on a concept where wire elements 154 are connected directly to the stent flares, either to form a common ring or to form a direct connection point. FIG. 14d illustrates how the wires 154 can be connected to the stent flare region (illustratively shown as long flare 104a comprised of a first wire 158a and second wire 158b). Here, the wire element 154 is placed in between a pair of wires comprising the stent flare, and a number of spot welds 156 are placed between the wire 154 and stent flare 104a to create the connection. The weld points 156 can be spaced out in different locations relative to the two wires forming the flare region 104a. Also, though the figure shows the wires forming flare region 104a connected at the same point along wire 154, this can be spread such that the first wire 158a sits at another point along wire element 154 compared to second wire 158b (e.g. 158a sitting further along element 154 as compared to 158b). Spreading out the wire and weld locations offers advantages in terms of spreading out high stiffness regions since the welded connection points will represent areas of high stiffness, in turn making deployment from the catheter and retraction back into the catheter easier.

Figure 14E:
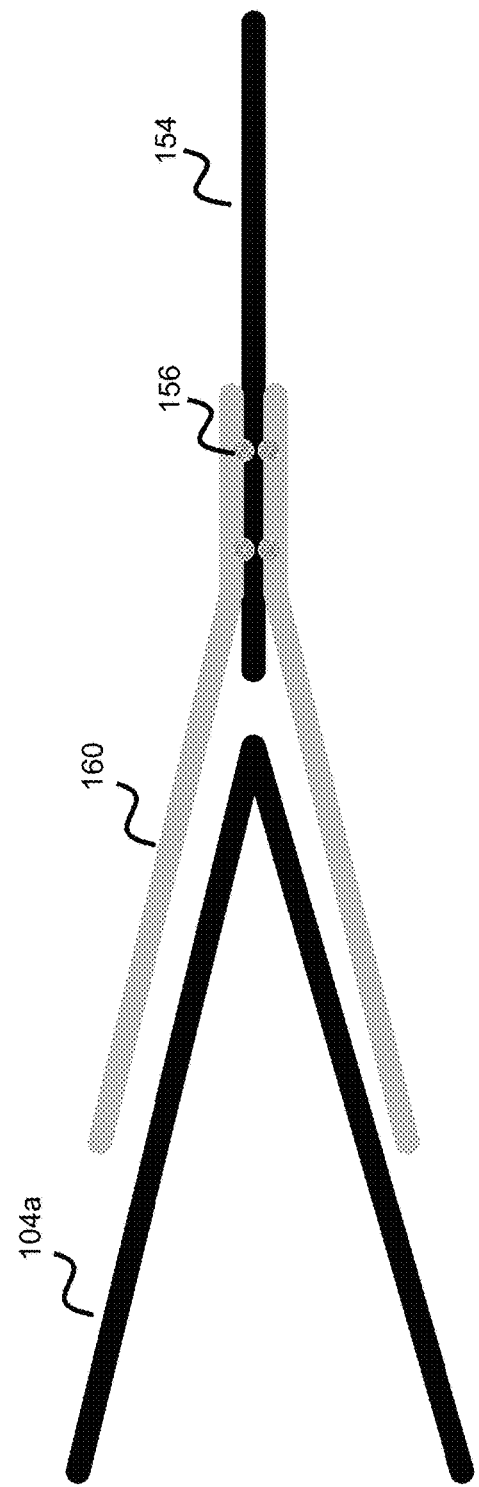

Please note, different stent flare embodiments are discussed earlier where some embodiments utilize a pair of wires converging to form a stent flare, and other embodiments utilize a single wire which creates a looped or flared end shape. In the latter concept, the wire comprising the flared loop 104a is cut to create a gap and the separate wire 154 would then be connected in this region. In another embodiment, this connection element is directly connected to the stent loop 104a such that two additional wires forming the "V" shape connect to the stent loop and wire element 154 is connected within this V-shape to compress the stent flare region down to a one wire element 154. The difference here is that the wire element 154 is connected to another crown element built over the stent flare 104a rather than the wire element 154 being directly connected to the stent flare. This configuration is best shown in FIG. 14e where loop 104a has element 160 built over it when then connects down to a single wire element 154.

The preceding description focused on the mandrel and/or frame, groove interface, and techniques used to create a stent having a common connection region at one end of the stent, where several wires condense down into a smaller group of wires forming a common connection region 121. The following description will discuss how the common connection region interacts with the delivery pusher to connect the stent to the delivery pusher.

Figure 15B:
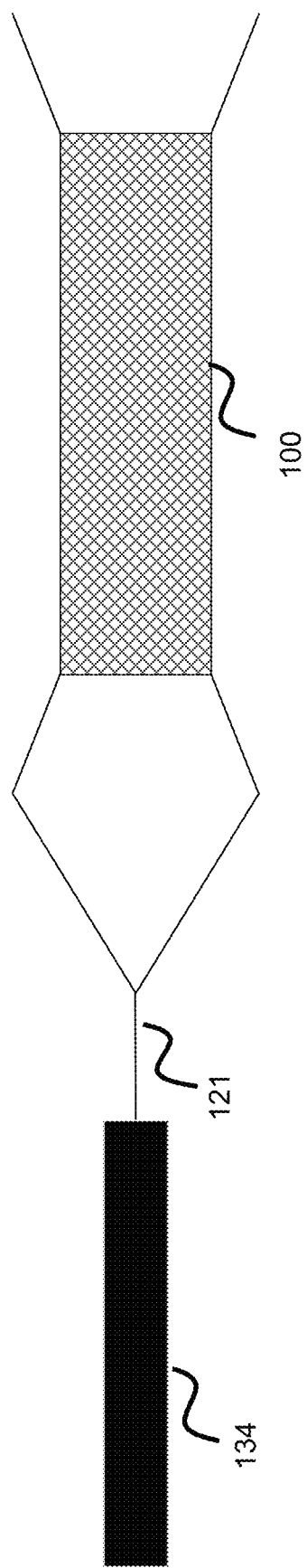
FIG. 15b illustrates a stent delivery system, according to one embodiment.

Stents are generally connected to a mechanical pusher, which takes the form of a rod or tube used to push the stent through a delivery catheter and to the target region. With the stents described herein which utilize a common connection interface, the stent 100 will taper down to a common connection interface 121, and this common connection interface 121 then connects to a pusher 134—as shown in FIG. 15a. FIG. 15b offers a similar view as FIG. 15a, except shows the stent flares in more detail and therefore represents a view of the stent, stent connection interface, and pusher when the stent is in its expanded state such that the flares radially project larger than the rest of the stent. The details of the connection between pusher 134 and stent common connection interface 121 is shown in more detail in FIGS. 16-18 and will be described.

Figure 18:
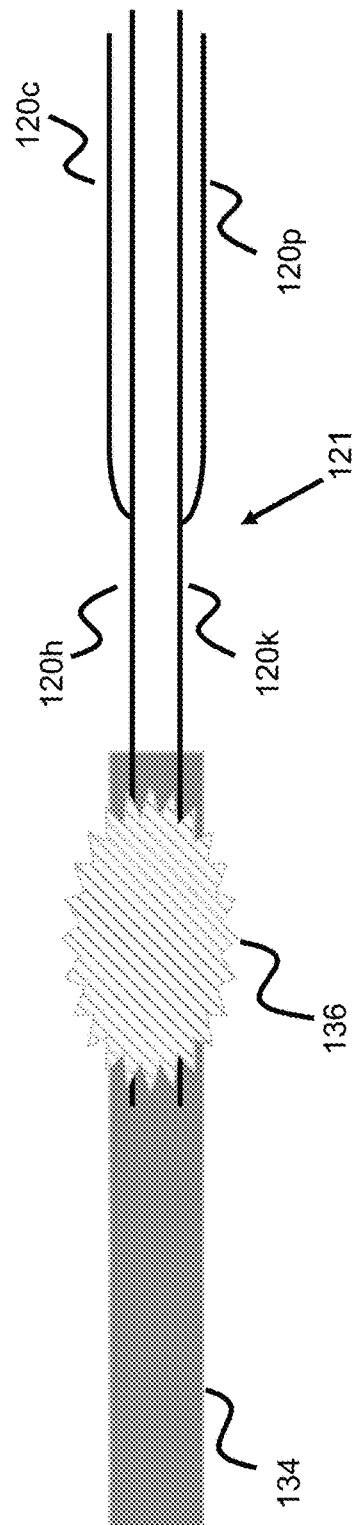

As shown in FIG. 16, the common connection interface/region 121 is comprised of the four wires 120c, 120h, 120k, 120p (which, as shown in FIG. 10, are condensed from the initial 8 loop/16 wire configuration). These four wires comprising the common connection interface 121, in turn, connect directly to the pusher 134. The pusher is a relatively long object and has a length corresponding to at least roughly the length of the delivery catheter since the pusher must be able to push the stent through the entire length of the delivery catheter and out of the delivery catheter to the target treatment site. FIGS. 16-18 can be thought of as showing the distal interface of the pusher 134 where the pusher is connected to the stent/stent connection interface. Some retention means 136—such as, for example, adhesive, solder, and/or a mechanical holder interface (e.g. ties, or an overlying cylinder enclosing the distal section of pusher 134 as well as common connection interface 121) is used to connect the pusher to the various wires. Detachment means commonly known to those skilled in the art—such as a thermolytic system utilizing heat to sever or degrade the holder interface 136, an electrolytic system, or a mechanical system (e.g., rotational threads) are used to detach the pusher from the stent once the stent is deployed in the vasculature thereby freeing the stent from the pusher.

The earlier description discussed the common connection interface 121 as comprised of four wires, but also mentioned how alternative wire arrangements could condense the common connection interface 121 down into two or even one wire. FIGS. 17-18 build on this concept to utilize a one-wire and two-wire pusher connection whereby the four wires further condense to a condensed wire structure.

An alternative embodiment is presented in FIG. 17 where the four wires normally forming the common connection interface intersect into one of the wires 120k, such that the one wire 120k is the only one connected to the pusher. In this example the other three wires are trimmed and affixed to wire 120k through adhesives, welding, ties, or other means so that only one wire is directly connected to pusher 134. Retention means 136, as discussed above, are used to connect the wire to the pusher 134, while a detachment system as described above is used to detach the stent from the pusher.

Another alternative embodiment is presented in FIG. 18, where the four wires normally forming the common connection interface 121 intersect into two wires which connect to pusher 134. Wire 120c attaches to longer wire 120h which connects to the pusher 134, and wire 120 attaches to longer wire 120k which is also connected to the pusher 134.

The attachments between wires can be created in a number of different ways as discussed earlier, including adhesives, ties, and welding (e.g., spot welding). Multiple spot welds in different locations along the length of the connected wires can be used to enhance the connection strength, or one weld point can be used to allow more flexibility between the two wires. Since the attachment locations will be somewhat stiff due to the presence of the attachment medium, the attachment points can be spread out or staggered along a particular wire (e.g. along a longer wire 120c which is one of the wires comprising common connection interface 121) to spread out the location of these locally stiffer areas.

Figure 19:
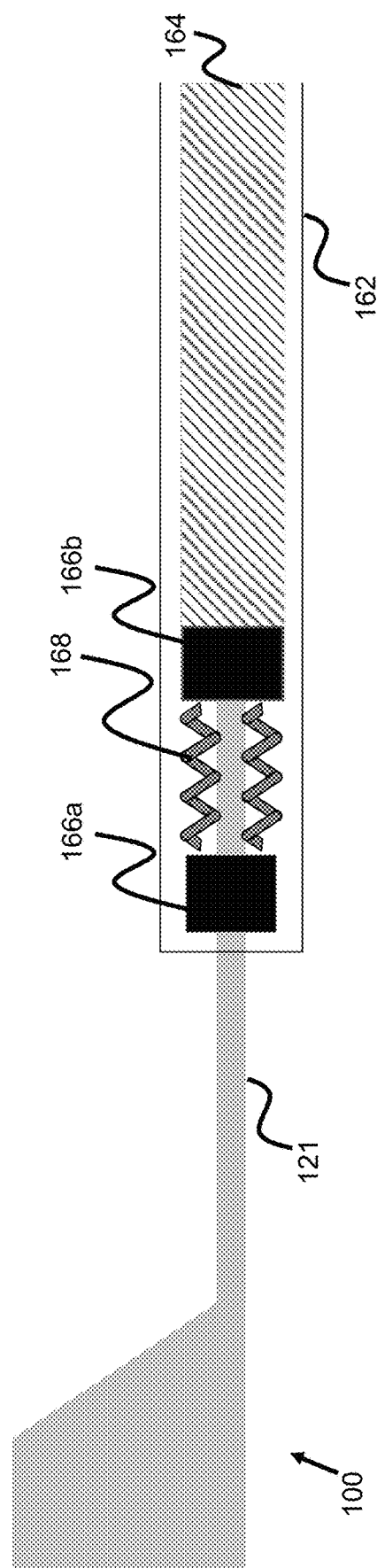
FIGS. 19-20 illustrate a stent delivery system, according to one embodiment.
Figure 20:
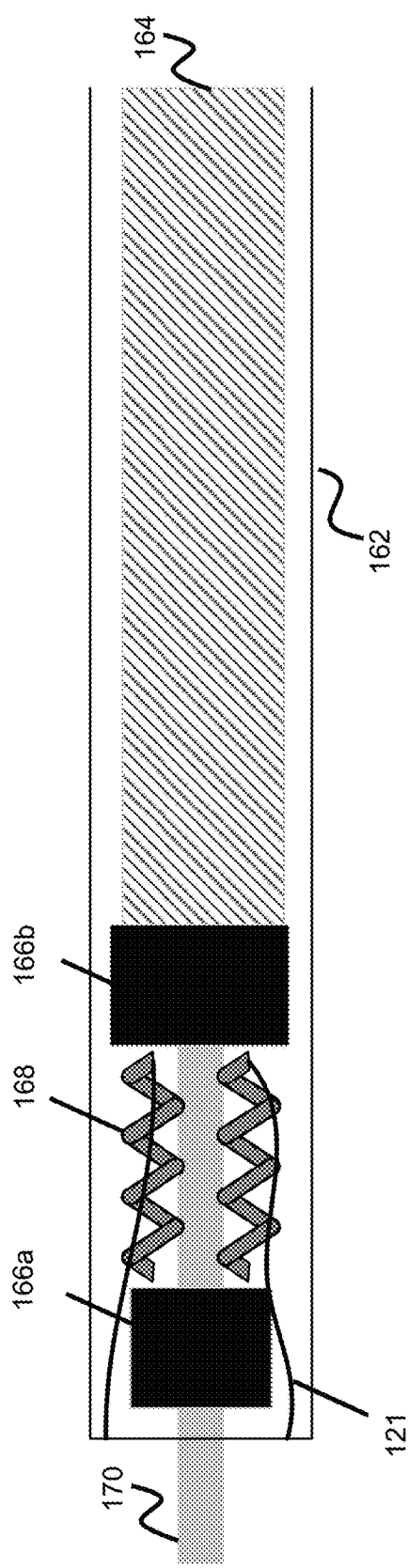

FIG. 19 shows another pusher system embodiment to keep a stent retained to a pusher system during delivery. The stent is originally contained within a delivery catheter 162. FIG. 19 shows the configuration after the stent 100 is pushed out from the catheter 162. Stent 100 is connected to a pusher 164 which is used to push the stent through the delivery catheter 162 and out of said delivery catheter 162. The distal part of the pusher includes two bands 166a and 166b, the bands can be radiopaque to aid in visualization and therefore can be considered marker bands; these marker bands sit along a core wire 170 that extends distally beyond the pusher 164—as best shown in FIG. 20. The common connection mechanism 121 connects to the stent, providing a connection interface with the pusher. A proximal portion of the common connection mechanism contains coils, these coils can be radiopaque to aid in visualization. Where the common connection mechanism comprises one or more wires, these coils are simply coiled over the wire/s and project from the wires such that the portion of the wires containing the coils are thicker than other portions of the wire comprising the common connection interface. Since the coil section is thicker, when placed between the two marker bands it fixes the stent in place (either completely, or only allowing a little give corresponding to whatever space is between the marker bands 166a, 166b and the marker coil 168) while the marker coil 168 is contained between the two marker bands 166a and 166b. As shown in the images, the length of the coil should be smaller than the gap between the two marker bands so that the coil is contained within the gap. In this way, the stent is connected to the pusher. The marker coil can take on the configuration shown with marker coil 106 of FIG. 2—with the caveat being that here the marker coil would be placed on the common connection interface. In one example, a coil is connected to only one of the one or more common connection mechanism wires which form common connection interface 121. In another example, a coil is connected to two common connection mechanism wires where one wire sits on either side of the marker band thereby providing a two-tiered connection interface—as best shown in FIG. 20. When the pusher 164 is pushed out of the delivery catheter 162, there is no longer a restraining force and the stent and common connection interface will expand thereby disengaging the binding marker coil 168 from the space between marker bands 166a, 166b.

Alternative embodiments similar to the deployment system of FIGS. 19-20 can utilize a coil-like common connection mechanism 121 where the coiled common connection mechanism adopts a first elongated shape when constrained within the delivery catheter 162, and adopts a second unrestrained coiled shape (its "heat-set"/"shape memory" shape) when freed from the delivery catheter. In this way, the common connection mechanism 121 shortens upon delivery thereby reducing the length of the wires hanging proximally off of the stent after delivery of the stent 100 as the common connection mechanism 121 adopts its non-elongated coiled delivery shape upon deployment from the catheter.

Figure 21:
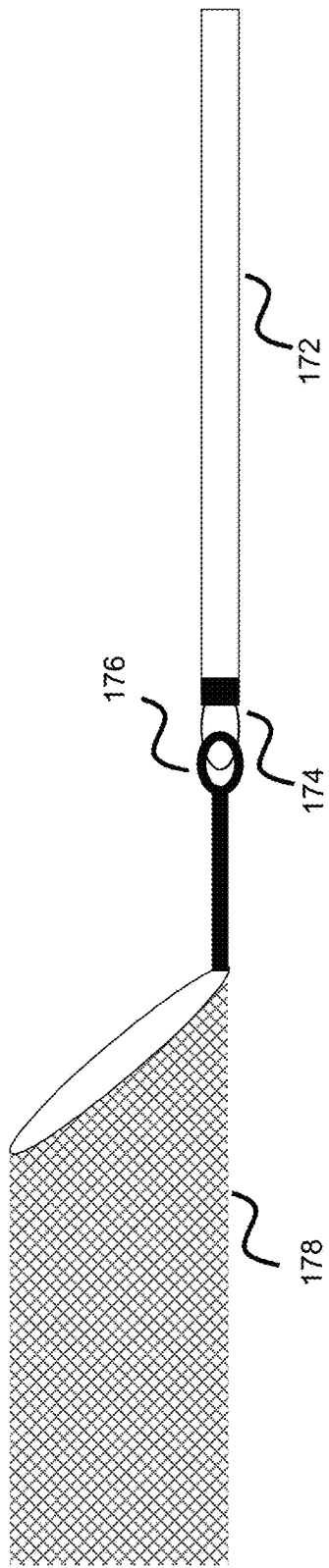
FIG. 21 illustrates a stent delivery system, according to one embodiment.

FIG. 21 shows an alternative embodiment where the pusher 172 ends in a ring-member 174, and stent 178 has a common connection member 176 which ends in its own ring-member 176. The two ring members (pusher ring member 174 and stent/common connection ring member 176) intersect in a jewelry chain-like manner. The pusher can utilize electrolytic or thermolytic means to sever the pusher ring member, thereby severing the pusher from the stent to deploy the stent 178. In one example, pusher ring member 174 is a thread or suture and an electrode placed along the pusher proximal of this thread/suture supplies the heat to sever the thread/suture to thereby release stent 178.

The earlier description discussed the use of certain metallic materials for potential use within the stent, such as nitinol or drawn-filled tubing. In some embodiments, particular parts of the stent, such as the stent flares and/or the common connection interface described earlier can utilize radiopaque wires or DFT to selectively aid in imaging in this particular region of the stent body.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A stent delivery system comprising:
a pusher used to deliver a stent, the stent having a plurality of proximally positioned end loops; and
a connection interface positioned between the pusher and the stent and proximally linked to the pusher and distally linked to the stent, the connection interface including:
a distal section having a plurality of wires, each of the plurality of wires connected to one of the plurality of end loops; and
a proximally adjacent section next to the distal section having less wires than the distal section, wherein the proximally adjacent section of the connection interface has half the number of wires than the distal section.

2. The stent delivery system of claim 1, wherein the connection interface further comprises a proximal end section connected to the pusher.

3. The stent delivery system of claim 2, wherein the proximal end section has one or two wires.

4. The stent delivery system of claim 1, wherein the plurality of proximally positioned end loops project radially outward.

5. The stent delivery system of claim 1, wherein the connection interface is independent of the stent and is mechanically attached to the stent.

6. The stent delivery system of claim 1, wherein the stent is composed of wires and each end loop is composed of two wires.

7. A stent delivery system comprising:
a pusher;
a stent delivered by the pusher, the stent having a plurality of proximally positioned end loops, wherein the plurality of proximally positioned end loops project radially outward; and a connection interface linking the pusher to the stent, the connection interface including:
  a distal section having a plurality of wires, each of the plurality of wires connected to one of the plurality of end loops; and
  a proximally adjacent section next to the distal section having less wires than the distal section.

8. The stent delivery system of claim 7, wherein the connection interface further comprises a proximal end section connected to the pusher.

9. The stent delivery system of claim 8, wherein the proximal end section has one or two wires.

10. The stent delivery system of claim 7, wherein the connection interface is independent of the stent and is mechanically attached to the stent.

11. The stent delivery system of claim 7, wherein the stent is composed of wires and each end loop is composed of two wires.

12. The stent delivery system of claim 7, wherein the proximally adjacent section of the connection interface has half the number of wires than the distal section.

13. A stent delivery system comprising:
a pusher;
a stent delivered by the pusher, the stent having n proximally positioned end loops where n is greater than 1; and
a connection interface linking the pusher to the stent, the connection interface including:
  a distal section having n wires, each of the n wires connected to end of the n end loops; and
  a proximally adjacent section next to the distal section having less than n wires;
wherein the connection interface is independent of the stent and is mechanically attached to the stent.

14. The stent delivery system of claim 13, wherein the proximally adjacent section of the connection interface has n/2 wires.

15. The stent delivery system of claim 13, further comprising a proximal end section next to the proximally adjacent section, where the proximal end section has n/4 wires.

16. The stent delivery system of claim 13, wherein the connection interface further comprises a proximal end section connected to the pusher.

17. The stent delivery system of claim 16, wherein the proximal end section has one or two wires.

18. A stent delivery system comprising:
a pusher used to deliver a stent, the stent having a plurality of proximally positioned end loops; and
a connection interface positioned between the pusher and the stent and proximally linked to the pusher and distally linked to the stent, the connection interface including:
  a distal section having a plurality of wires, each of the plurality of wires connected to one of the plurality of end loops; and
  a proximally adjacent section next to the distal section having less wires than the distal section;
wherein the connection interface is independent of the stent.

19. A stent delivery system comprising:
a pusher used to deliver a stent, the stent having a plurality of proximally positioned end loops; and
a connection interface positioned between the pusher and the stent and proximally linked to the pusher and distally linked to the stent, the connection interface including:
  a distal section having a plurality of wires, each of the plurality of wires connected to one of the plurality of end loops; and
  a proximally adjacent section next to the distal section having less wires than the distal section;
wherein the connection interface is mechanically attached to the stent.

* * * * *